United States Patent [19]

Wilson et al.

[11] Patent Number: 5,849,284
[45] Date of Patent: Dec. 15, 1998

[54] BIOLOGICAL CONTROL OF MOLLUSCS WITH DAUER LARVAE OF *PHASMARHABDITIS NEMATODES*

[75] Inventors: Michael John Wilson; David McKellar Glen, both of Bristol; Jeremy David Pearce, West Sussex, all of Great Britain

[73] Assignee: Agricultural Genetics Company Ltd., Cambridge, Great Britain

[21] Appl. No.: 625,018

[22] Filed: Mar. 29, 1996

Related U.S. Application Data

[62] Division of Ser. No. 178,294, Mar. 8, 1994, Pat. No. 5,527,525.

[30] Foreign Application Priority Data

Jul. 11, 1991 [GB] United Kingdom .................... 9115011

[51] Int. Cl.$^6$ .......................... A01N 63/00; A01N 25/00; C12N 1/20; C12N 1/00
[52] U.S. Cl. ..................... 424/93.1; 424/93.47; 424/405; 435/252.1; 435/822
[58] Field of Search ................................ 424/93.1, 93.47, 424/405; 435/252.1, 822

[56] References Cited

FOREIGN PATENT DOCUMENTS 9 100 012  1/1991  WIPO .

OTHER PUBLICATIONS

Godan, D., "Pest Slugs and Snails: Biology and Control", Springer–Verlag, Berlin Heidelberg New York, 1983.

Andrassy, I., Taxonomic Review of the Sub–Order Rhabditina (Nematoda: Secernentia), 1983, Orston, Paris, pp. 84–117.

Glen, D.M., & C.W. Wiltshire, "Estimating Slug Populations From Bait–Trap Catches", 1986 British Crop Protection Conference—Pests and Diseases, pp. 1151–1158.

Bedding, R.A., "Large scale production, storage and transport of the insect–parasitic nematodes Neoaplectana spp. and Heterorhabditis spp.", Ann. Appl. Biol., 104, 1984, pp. 117–120.

Bedding, R.A., "Low Cost In Vitro Mass Production of Neoaplectana and Heterorhabditis Species (Nematoda) for Field Control of Insect Pests," Nematologica, 27, 1981, pp. 109–114.

Poinar, Jr., G.O. & E.L. Hansen, "Associations between Nematodes and Bacteria," Helminthological Abstracts (Series B), vol. 55, No. 3, Sep. 1986, pp. 61–81.

"Morphology and Biology of Bostryx Consperus (Sowerby) (Mollusca, Bulimulidae) in the Central Costal Slopes of Peru", R. Ramirez, Revista Brasileira De Zoologia, vol. 5, No. 4, 1988, pp. 609–617.

"Nematoden und Schnecken", H. Mengert, Zeitschrift Fur Morphologie Und Okologie Der Tiere, vol. 41, 1953, pp. 311–349.

"Nematodes–Bacteries, une Association Efficace Dans La Lutte Contre Les Insectes", C.Douenel, Biofutur, No. 64, Jan. 1988, pp. 39–42.

Japanes Abst. (JP 63313580), "Formate Dehydrogenase–prod by news *Moraxella*. . . ", 1987, see abstract.

*Primary Examiner*—David M. Naff
*Assistant Examiner*—Deborah K. Ware
*Attorney, Agent, or Firm*—McDermott, Will & Emery

[57] ABSTRACT

The invention disclosed is related to a composition for the control of molluscs wherein an effective amount of infective dauer larvae of *Phasmarhabditis nematodes* which have been cultured with a nematode growth promoting and pathogenicity-inducing bacterium, as well as a carrier or encapsulation agent are provided as the ingredients for the composition. Further, the composition can be used in the form of a water-dispersable powder comprising as the carrier a calcium montmorillonite clay. The nematode concentration in the water-dispersable powder is $0.1 \times 10^6$ to $2.0 \times 10^6$ per gram of total composition (wet weight), and preferably from $0.3 \times 10^6$ to $0.8 \times 10^6$ per gram of the total composition (wet weight). Further, the nematodes are selected from amongst the species *P. neopapillosa* or *P. hermaphrodita*. The growth promoting bacterium is a *Moraxella osloensis* strain or *Pseudomonas fluorescens* strain.

7 Claims, 3 Drawing Sheets

BIOLOGICAL CONTROL OF MOLLUSCS WITH DAUER LARVAE OF *PHASMARHABDITIS* NEMATODES

This application is a division of application Ser. No. 08/178,294 filed Mar. 8, 1994, now U.S. Pat. No. 5,527,528.

This invention relates to the control of agricultural and horticultural pests and more particularly to the control of molluscs, including slugs, e.g. *Deroceras reticulatum* and snails, e.g. *Monacha cantiana*. For convenience, the invention will be described mainly in relation to slug control but it is to be understood that it is also applicable to the control of other molluscs that are harmful to plants in the field or greenhouse, or which carry parasites harmful to humans or animals.

Slugs are a widespread pest of several major agricultural crops, particularly winter wheat, oilseed rape and potatoes in the UK, other European countries, north and central America and Australasia. They are also a problem in horticulture and to the domestic gardener. The most economically important slug species is the grey field slug, *Deroceras reticulatum* (family: Limacidae), although other limacid slugs and Arion (family: Arionidae), Tandonia, Milax (family: Milacidae) and Boettgerilla species also can cause significant damage. Snails also can be a pest problem in horticulture and agriculture, one example being *Monacha cantiana* (family: Helicidae). Examples of mollusc pests are listed by Godan in "Pest Slugs and Snails" (1983, Springer-Verlag, Berlin). Molluscs may also carry pests which represent a hazard to human or animal health. Examples include Lymnaea species (family: Lymnaeidae), which carry the liver fluke *Fasciola hepatica*, and Bulinus species (family: Bulinidae) which carry *Opisthorcis sinensis*. The families Limacidae, Arionidae, Milacidae and Helicidae are members of the Order Stylommatophora. The families Bulinidae and Lymnaeidae are members of the Order Basommatophora.

Current methods of control are only partially effective and the available chemicals are highly toxic to birds and mammals. Hence there is a clear need for more effective, more persistent and less toxic methods of mollusc control.

It has now been discovered that nematodes of the genus Phasmarhabditis are effective control agents for a wide range of mollusc species. Particularly effective Phasmarhabditis species are the related organisms *P. neopapillosa* and *P. hermaphrodita* which will be described further hereinafter. These species have been known for many years and are described in the literature, having been characterised especially by Andrassy in "A Taxonomic Review of the Sub-Order Rhabditina (Nematoda: Secementina)" (1983. Orstom, Paris). However, the biological activity of these organisms against slugs and other mollusc pests has not hitherto been recognised.

The present invention therefore comprises the use of Phasmarhabditis species for the control of agricultural and horticultural pests or human and animal health pests, especially molluscs. The organisms can be obtained from slugs in the field and cultured by methods described hereinafter to produce amounts sufficient for formulation into suitable compositions for application in the field or greenhouse. Typical compositions for practical use utilise acceptable carrier materials such as peat, clays, and other solids or semi-solid carriers such as gel materials. Outdoor microplot and field trials have shown that the nematode can both kill slugs and protect Chinese cabbage seedlings and wheat seeds or seedlings from slug damage at least as well as, or better than, methiocarb, the best chemical currently available.

Biology of the Organism

The nematode was isolated from slugs collected at Long Ashton Research Station in Great Britain. The nematode was found to be associated with a fatal disease in slugs with characteristic symptoms, most noticeably a swelling of the slug's mantle. The nematode was identified as belonging to the Sub-Order Rhabditina and further identified using a key (Andrassy, 1983). The main taxonomic characteristics of this group are the mouthparts and the male reproductive structures. The nematodes isolated at Long Ashton had a distinctive, short stoma with an isomorphic metastom, and males, when present, had peloderan bursas, fitting the genus Phasmarhabditis. Andrassy (1983) lists two species which are morphologically identical to these nematodes but are separated from each other on the basis of the number of males present in the populations. In *Phasmarhabditis neopapillosa* males and females are equally abundant, whereas in *P. hermaphrodita* males are extremely rare. It is not yet known whether *P. hermaphrodita* is a separate species or just a biological variant of *P. neopapillosa* (Andrassy 1983). *P. hermaphrodita* was first described by Maupas, in Archives de Zoologie (1900), Vol 8 pp 464–624, who named the nematode *Rhabditis caussaneli*. He found resistant larval forms in the intestine of *Arion ater* which he collected in Normandy. He maintained cultures of the nematode on rotten flesh for two years. He found that the adult worms were predominantly protandrous autogamous hermaphrodites. Males were present in very small numbers (1 male for 1300 females) and the number of males in cultures was not affected by nutritional conditions. Maupas never witnessed males mating with the females, which showed no change in their fecundity, or the sex ratio of their offspring in the presence of males. Maupas did not consider this nematode to be a parasite of slugs.

*Phasmarhabditis neopapillosa* was described by Mengert, who named the nematode *Rhabditis neopapillosa*, in Zeitschrift fur Morphologie und Okologie Tiere (1953), vol 41. pp 311–349 in his studies on the relationships between nematodes and terrestrial molluscs. He found the nematode as resistant larval stages ('dauer larvae') in the hind gut of the slug *Limax cinereoniger*. Mengert considered *P. neopapillosa* to be a saprophyte which thrives on decaying material for many generations, but when conditions become unfavourable the juveniles fail to mature and form resistant non-feeding dauer larvae. He considered the lifestyle of *P. neopapillosa* to be identical to two other species, *Phasmarhabditis papillosa* and *P. hermaphrodita*. He considered that the dauer larvae of these three species wander, when the opportunity arises, into the body of slugs where they remain as dauer larvae until the slug dies, after which they develop and reproduce, feeding on the corpse. Mengert thought that the stay in the slug was not a necessary part of the nematode life cycle but he considered that the dauer larvae of these species did show a degree of adaptation to life within slugs. However, he stated that they are not parasites of slugs.

Nematodes can be isolated from slugs collected from the field using bran baited traps left in an area of rough grassland. Once collected the nematodes can be isolated from the slug's gut or mantle cavity following dissection. Many species of nematodes are associated with slugs (Mengert, 1953) and it is necessary to confirm the identification of *P. hermaphrodita* and *P. neopapillosa* using a taxonomic key (Andrassay, 1983). If only infective stage nematodes (dauer larvae) are found in the slug it is necessary to culture the nematodes in order to identify them.

*Phasmarhabditis* nematodes have been isolated at Long Ashton on a number of occasions. In some cases the population of nematodes consisted of males and females, whereas in other cases the populations consisted of hermaphrodites only. Nematodes from both types of population were examined using light microscopy and scanning electron microscopy. Protein profiles from the different populations also were examined following separation of proteins by iso-electric focusing. No differences between populations were found using any of the above methods. The isolated nematodes correspond to the available descriptions of both *P. neopapillosa* and *P. hermaphrodita*.

*Phasmarhabditis* nematodes can be produced by methods to be described in this specification. It is already known in the art that insect parasitic nematodes can be produced on a large scale for commercial use by liquid culture, using stirred tank or airlift fermenters, or by solid culture in bags or trays of foam chips. Similar techniques can be used for large scale production of *P. hermaphrodita* or *P. neopapillosa*. Thus the nematode used in accordance with this invention is readily cultured on kidney-based medium in foam chips or in liquid culture, using similar techniques to those used for production of insect parasitic nematodes. For the purposes of the present invention it is recommended that the culture of nematodes is harvested at the dauer larvae stage.

Requirement for Associated Bacteria

Figure 1:
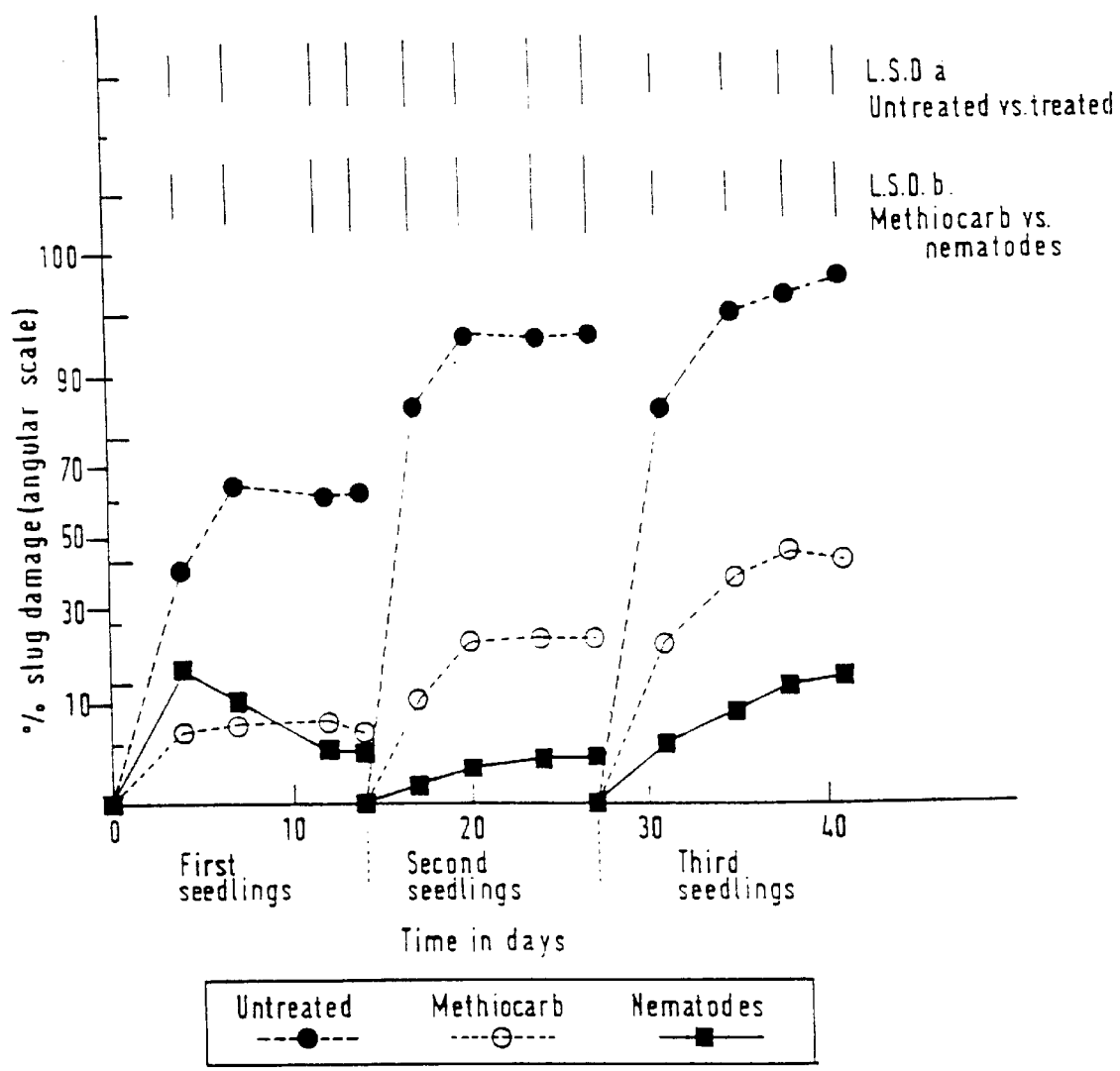
FIG. 1 is a graph illustrating the use of *Phasmarhabditis* nematodes to control plant damage by field slugs.

*Phasmarhabditis* nematodes are bacterial feeders. Many bacterial isolates have been found to be associated with *Phasmarhabditis* nematodes after isolation from moribund slugs. We have investigated the relationship between the nematode and these associated bacteria in order to determine which bacteria can support good nematode growth and to compare the pathogenicity of nematodes reared on different species of bacteria.

In order consistently to produce high yields of *Phasmarhabditis* nematodes which are pathogenic to molluscs it is preferable to grow them in cultures with one known associated bacterium (monoxenic cultures) and so a method of selecting individual species of bacteria capable of supporting nematode growth is needed. Bacteria capable of supporting nematode growth can be isolated from within nematodes, from nematode cultures growing on a mixed microbial population, from slugs infected with bacteria and from slug corpses infested with the nematodes. Nematodes can then be freed from all contaminating bacteria, and introduced into cultures with the different individual species of bacteria. Incubation of these cultures allows the selection of bacterial isolates capable of supporting nematode growth.

Approximately 100 bacterial isolates have been obtained from the nematodes, from slugs infected with nematodes and from dead slugs infested with nematodes, 15 of which have been tested for their ability to support nematode growth. Of these, 9 isolates, representing 8 species, were found to support good nematode growth on agar. The 8 species of bacteria, which were found to support good nematode growth are as follows:

*Pseudomonas fluorescens*
*Providencia rettgeri*
*Serratia proteomaculans*
*Aeromonas salmonicida*
*Moraxella osloensis*
*Bacillus cereus*
*Flavobacterium odoratum*
*Flavobacterium brevi*

The ability of nematodes reared on different species of bacteria to kill slugs can be tested in a bioassay. In such a bioassay slugs are exposed to different numbers of nematodes and the resulting slug mortality is recorded. Using this method, quantitative measures of pathogenicity (e.g. $LD_{50}$) of nematodes against slugs can be obtained and used to compare the pathogenicity of nematodes reared on different species of bacteria. It is important that the nematode is supplied in association with specific bacteria because bacteria are essential not only for growth of the nematode (both in vitro and in vivo) but also for their ability to kill slugs. The nematode carries associated bacteria on entry into the slug thus allowing rapid establishment and multiplication of the nematode leading to the death of the slug.

Examples of suitable bacterial strains are *Moraxella osloensis* strain 48 and *Pseudomonas fluorescens* strain 141, samples of which have been deposited under the Budapest Treaty with the National Collection of Industrial and Marine Bacteria* under Accession Numbers NCIMB 40508 and NCIMB 40509 respectively, on 9 Jun. 1992. The strain *Pseudomonas fluorescens* 141 is a gram negative oxidase positive, catalase positive bacterium which is non-motile and scores negative in the O/F (Hugh and Leifson) test for aerobic or anaerobic breakdown of glucose. The strain *Moraxella osloensis* 48 is a gram negative, oxidase positive, catalase positive bacterium which is non-motile and scores negative in the O/F (Hugh and Leifson) test. Biochemical profiles of both strains on standard substrates (API ZONE test strip) is shown below.

*Address: 23 St. Machar Drive, Aberdeen, AB2 1RY, United Kingdom

| Reaction | *Moraxella osloensis* 48 | *Pseudomonas fluorescens* 141 |
|---|---|---|
| $NO_3$—$NO_2$ | + | − |
| $NO_3$—$N_2$ | * | − |
| Indole | − | − |
| Acid from glucose | − | − |
| Arginine dihydrolase | − | + |
| Urease | − | − |
| Esculin hydrolysis | − | − |
| Gelatin hydrolysis | − | + |
| β Galactosidase | − | − |
| Assimilation of: | | |
| Glucose | − | + |
| Arabinose | − | + |
| Mannose | − | + |
| N-acetylglucosamine | − | + |
| Maltose | − | − |
| Gluconate | − | + |
| Caprate | − | + |
| Adipate | − | − |
| Malate | − | + |
| Citrate | + | + |
| Phenyl acetate | − | − |

* = not tested

Useful variants of *M. osloensis* strain 48 and *P. fluorescens* strain 141 may be obtained by repeated sub-culturing of pure cultures of these strains. Variants may also be obtained either by re-isolating bacteria from *Phasmarhab-*

*ditis nematodes* previously grown in association with either of the strains or by re-isolating bacteria from slugs infected with nematodes. Such variants may have incurred genotypic or phenotypic changes as a result of environmental influences or selective pressure. Useful derivatives of *M. osloensis* strain 48 and *P. fluorescens* strain 141 may be constructed by the introduction of DNA coding for desirable attributes from other organisms. Methods for introduction of foreign DNA into bacteria are well known to those skilled in the art and include techniques such as plasmid transfer, transduction and transfection. Useful mutants of *M. osloensis* strain 48 and *P. fluorescens* strain 141 may be obtained by mutagenesis using methods, well known to those skilled in the art, such as chemical (eg nitrosoguanidine), physical (ultraviolet light) and genetic (transposon mutagenesis) techniques. Such variants, derivatives and mutants of the strains may be altered with respect to characteristics such as growth rate or the ability to grow on certain food sources but will retain the essential characteristics relevant to this invention ie the ability to both support growth of *Phasmarhabditis nematodes* and to induce pathogenicity towards molluscs.

For use in control of agricultural pests, nematodes are harvested from fermenters by centrifugation, filtration or settling under gravity. The nematodes are washed to remove spent medium components and either formulated immediately or stored as cooled, aerated aqueous suspensions prior to subsequent formulation. Nematodes can be formulated for agricultural use as aqueous suspensions, on solid carriers such as charcoal, clays, peat, vermiculite or polyetherpolyurethane sponge, or encapsulated in gels such as alginate or polyacrylamide. A particularly desirable formulation contains desiccated or partially-desiccated nematodes. The formulated nematodes can be applied for control of pests by forming an aqueous suspension and applying this to the area to be treated by spray, irrigation or drench.

EXAMPLE 1

Method for Isolation of *Phasmarhabditis nematodes*

Living nematodes extracted from slugs collected from the field using bran baited traps are placed on kidney-based agar medium made by mixing 10% homogenised pig kidney, 3.5% corn oil, 2% agar and 84.5% water (% by weight) which is then sterilised by autoclaving and poured into petri dishes. The medium encourages the growth of the bacteria associated with the nematodes. The nematodes feed on these bacteria and grow and reproduce on the plates.

EXAMPLE 2

Isolation of Bacteria Associated with Nematodes or Nematode-Infected Slugs

Bacteria associated with nematodes or nematode-infected slugs can be isolated by any of the following methods:

(i) Isolation of bacteria from within nematodes

Nematodes are surface sterilised by immersion in 0.1% (w/v) sodium ethylmercurithiosalicylate (Thimerosal) for 1 hour then transferred to fresh Thimerosal for a further three hours. Bacteria can be liberated from nematodes using sterile microbiological techniques in either of two ways:

a) Individual nematode larvae are transferred to a drop of sterile saline on a flame sterilised microscope slide. The nematodes are then cut at several sites along the length of their bodies. The drop of saline complete with nematode corpse is then transferred using a sterile pasteur pipette to a 9 cm petri dish of nutrient agar where it is spread over the surface using an alcohol-flamed glass spreader.

b) Many surface sterilised nematodes are suspended in 1 ml of sterile Ringer's solution which is transferred to a 5 ml teflon tissue homogeniser. The nematode suspension is ground and then transferred to 9 ml of sterile nutrient broth. The broth is shaken vigorously and serial dilutions are made. 0.1 ml aliquots of each dilution are placed onto plates of nutrient agar and spread using a glass spreader and incubated. After 48 hours incubation at 25° C., different bacterial isolates can be selected on the basis of colonial morphology and subcultured using standard microbiological techniques.

(ii) Isolation of bacteria from xenic foam chip cultures

Foam chips containing nematodes and bacteria are taken from thriving xenic cultures using alcohol-flamed forceps. Each chip is put into a tube containing 10 ml sterile nutrient broth and agitated. Serial dilutions of the resulting bacterial/nematode suspension are made and 0.1 ml aliquots of different dilutions are spread on nutrient agar plates and incubated.

(iii) Isolation of bacteria from live slugs infected with nematodes

*P. hermaphrodita/P. neopapillosa* infects and multiplies in the mantle region of slugs and it is from within this region that bacteria can be isolated. The mantle is first swabbed with dry cotton wool buds to remove as much slime as possible. The surface of the mantle then is swabbed with 70% (v/v) ethanol to surface-sterilise the mantle. A flame-sterilised mounted needle is used to pierce the mantle then drops of fluid on the end of the needle are transferred directly to nutrient agar plates where they are spread using a glass spreader and incubated.

(iv) Isolation of Bacteria from Dead Slugs

Smears of tissue from slug corpses which have died following nematode infection and are covered in nematodes are suspended in nutrient broth using a bacteriological loop. Serial dilutions are made from this suspension and 0.1 ml aliquots spread onto nutrient agar plates and incubated.

EXAMPLE 3

Method for Selecting Bacteria which Support Good Nematode Growth

Before it is possible to screen different bacteria for the ability to support nematode growth it is first necessary to obtain nematodes free from bacteria. The female reproductive tract of nematodes is generally sterile (Poinar and Hansen, Helminthological Abstracts. Series B [1986] Vol 55 No 3 pp 61–81) and thus J1 juveniles immediately after hatching are sterile. Individual gravid adult nematodes selected from nematode cultures or slugs are transferred to a sterile watch glass containing 0.02% (w/v) Thimerosal, where they are left overnight at 10° C. During this time eggs hatch within the adults and the juveniles (J1) are released. The following day the juveniles are transferred by pipette to centrifuge tubes filled with 10 ml of quarter strength Ringers solution containing 500 units/ml penicillin G and Streptomycin sulphate. The juveniles are kept in this solution for a further 24 hours at 10° C. They are then concentrated by gentle centrifugation (50×G for 10 minutes), collected from the bottom of the tube, resuspended in fresh sterile quarter strength Ringer's solution and spun down again. The resuspension and centrifugation is repeated once more to remove any traces of antibiotics. The larvae are then placed in a sterile watch glass. The nematodes can then be handled individually using micro-pipettes made by drawing out dropping pipettes in a bunsen flame to a width of approximately 0.1 mm. Nematode cultures are grown on kidney agar (as described in Example 1) in 3 cm petri dishes. One bacteriological loopful of 18 hour nutrient broth culture of the bacteria to be tested is streaked over one half of the 30 mm kidney plates. Ten axenic juvenile nematodes, obtained as described in Example 8, are added at the edge of the petri dish in the half without bacteria, so that nematodes have to move at least 15 mm across a bacteria-free surface before reaching the test bacterium. The plates are incubated at 15° C. Any bacteria present with the nematodes which have not been killed during the axenisation process form visible colonies on this halt of the plate and the plates can be discarded. After one week, plates showing bacterial contamination in the "clean" half are discarded. After two weeks the numbers of nematodes present on plates can be counted by direct microscopic examination; the lid of the petri dish is removed and replaced with another lid previously marked with a counting grid. After three weeks nematodes can be counted again by flooding nematodes off the agar in a known volume of water and counting the numbers present in the resulting suspension using a Peter's 1 ml counting chamber.

Nine different species of bacteria collected using the methods described were screened for their ability to support nematode growth. The results are shown in Table 1.

TABLE 1

Numbers of *Phasmarhabditis* nematodes per petri dish after two and three weeks growth in monoxenic culture with different bacteria. Data were transformed to logarithms for statistical analysis.

|  | Week 2 | | Week 3 | |
| --- | --- | --- | --- | --- |
| Bacterium | Numbers | Log | Numbers | Log |
| Axenic | 2 | 0.41 | 0 | 0.00 |
| Bacterium 1A | 170 | 2.18 | 18090 | 4.22 |
| Bacterium 17 | 0 | 0.04 | 0 | 0.00 |
| Bacterium 34 | 1 | 0.13 | 890 | 1.00 |
| Bacterium 48 | 60 | 1.70 | 54060 | 4.73 |
| Bacterium 54 | 80 | 1.53 | 25950 | 4.39 |
| Bacterium 77 | 1160 | 3.06 | 86340 | 4.93 |
| Bacterium 83 | 520 | 2.46 | 67000 | 4.78 |
| Bacterium 141 | 690 | 2.77 | 75220 | 4.85 |
| Bacterium 156 | 250 | 2.26 | 83630 | 4.89 |

S.E.D. for comparing log. nematode numbers = 0.204, 128 D.F.

After three weeks there were highly significant ($P<0.001$) differences in the ability of the bacteria to support nematode growth.

EXAMPLE 4

Method for Mass Cultivation of *Phasmorhabditis* nematodes by Foam Chip Culture

The nematodes can be mass cultured on polyether polyurethane foam chips using techniques similar to these developed for mass rearing insect parasitic nematodes (Bedding, in Nematologica (1981), vol 27, pp 109–114 and Annals of Applied Biology (1984), vol 104, pp 117–120). The medium consists of 65% pigs kidney, 15% beef dripping and 25% water (% by weight). The kidney is chopped into small pieces, the water is added then the mixture is 'liquidized' in a Waring blender. The beef dripping is melted in a large pan over a gas ring then the kidney homogenate is added and mixed thoroughly with the tat and cooked until brown. The mixture is then returned to the Waring blender and ground once again. This mixture is then mixed with foam chips, with 12 parts by weight of medium being added to 1 part foam chips. This medium can be dispensed into conical flasks, or autoclave bags as described by Bedding (1984). Foam chip cultures are inoculated with nematodes and bacteria simultaneously. Each bag is slit open at the top and 75 ml of an overnight culture of bacteria is added. The bacterial culture can be in the form of a mixed microbial population, obtained as described in Example 2, or as a pure culture of a bacterial strain selected for the ability to support good nematode growth as described in Example 3. Nematodes on agar from petri-dishes or on foam chips from previous bag cultures are added. Culture bags are incubated at 15° C. for three weeks after which time many infective juveniles can be seen on the inside of the bags, having left the spent medium. Nematodes are harvested from the foam chips by a modified funnel extraction technique, similar to that used for collecting nematodes from soil samples. 17.5 cm diameter copper soil sieves are lined with a 17.5 cm milk filter and placed in 50 cm flower-pot saucers. The foam chips from the bags are placed in the sieves to a depth of approximately 2 cm and the flower-pot saucers are filled with water until the water level just reaches the bottom of the foam chip layer. The sieves are then left overnight during which time live nematodes swim through the milk filters and collect in the water below. After cleaning the nematode suspension of spent medium and bacteria by changing the water several times, the nematodes are stored in aerated water at 10° C. until they are required.

EXAMPLE 5

Liquid Culture of Monoxenic *Phasmarhabditis* nematodes

Axenised nematodes were cultured on a solid medium (kidney based) with the appropriate bacteria. After 3 weeks the nematodes were transferred to liquid culture.

The nematodes were grown in shake flask culture under the following conditions:

Medium—10% kidney, 1% yeast extract, 3.5% corn oil.

Flask—250 ml conical flasks with 50ml of medium.

Temperature—15° C.

Shaker speed—200 rpm.

The flasks were inoculated with 1 ml of a bacterial species grown in nutrient broth. After 24 hours the nematodes were washed into the flasks with sterile tap water and incubated for three weeks.

The nematodes were washed twice with sterile water and counted. The nematodes were then used as inoculum for culture experiments. Nematodes were added to culture flasks at the rate of 3000 nematodes/ml to flasks pre-inoculated with bacteria.

The nematode was cultured with 4 different bacteria. Nematode counts were carried out at different times during the culture period. *Dauer larvae* (also known as infective juveniles) were assessed as nematodes with a retained second stage cuticle.

Nematodes were counted after 20 days incubation and the results are expressed in Table 2.

TABLE 2

Liquid culture of monoxenic nematodes

| | Mean no of nematodes per ml | | |
| --- | --- | --- | --- |
| Bacterium | No of Replicates | Dauer Larvae | Other Stages |
| P. fluorescens | 6 | 1220 | 110 |
| S. proteomaculans | 6 | 11500 | 7400 |
| P. rettgeri | 6 | 99900 | 189000 |
| M. osloensis | 3 | 72000 | 223000 |

Mass production of the nematode by liquid culture in large scale fermentation vessels, based on the conditions described in this Example, can be achieved easily by those skilled in the art.

EXAMPLE 6

Method for Selecting Bacteria Which Confer Pathogenicity Against Slugs

Nematodes grown in monoxenic culture with two species of bacteria, *Providencia rettgeri* and *Moraxella osloensis*, as described in Example 5, were tested for pathogenicity against the slug *Deroceras reticulatum*. Plastic boxes (135× 75×50 mm) were filled with 440 g air-dried soil aggregates, 12.5–25 mm in diameter, which had been obtained by sieving. The soil aggregates from each box were removed and soaked in 80 ml of water.

Untreated boxes without added nematodes and boxes treated with five nematode doses (15000, 23000, 35000, 55000 and 75000 nematodes per plastic box) were used. Two replicate boxes were used for all six treatments for both batches of monoxenic nematodes.

The nematodes were counted and the appropriate number suspended in 50 ml of tap water. The aggregates were replaced in the box and the nematode suspension was distributed evenly over the surface of the aggregates layer by layer. Ten *D. reticulatum* were placed between the middle layers of each box. 50 ml of tap water was distributed evenly over the aggregates in the boxes without added nematodes so that the final moisture content in each box was approximately 30% (w/w).

The slugs were kept in the soil for a five day infection period at 10° C. after which they were removed and transferred to Petri dishes where they were kept individually and fed discs of Chinese cabbage leaves. After a further nine days at 10° C. (fourteen days after initial exposure to the nematodes), the numbers of dead and living slugs were recorded. Mortality data were corrected for background mortality as seen in the untreated boxes. Corrected mortality data were plotted against nematode dose for nematodes grown in monoxenic culture with both bacteria.

In this experiment nematodes grown with *M. osloensis* and *Pr. rettgeri* were pathogenic to *D. reticulatum*. This method can be used to select other strains of bacteria, e.g. *P. fluorescens* strain 141, which confer pathogenicity against slugs.

EXAMPLE 7

Formulation of *Phasmarhabditis* nematodes

Monoxenic *Phasmarhabditis* nematodes, which had been grown in association with *M. osloensis* strain 48 as described in Example 5, were harvested by centrifugation and washed in water by a repetitive process of settling and resuspension in fresh water until the nematodes were free of residual growth medium. The washed nematodes were concentrated by centrifugation to produce a nematode aqueous paste which contained in the range of $0.1 \times 10^6$ to $2.0 \times 10^6$ nematodes per gram of paste. The nematode paste was mixed with a calcium montmorillonite clay to produce a water-dispersable powder composition containing from $0.05 \times 10^6$ to $1.8 \times 10^6$ nematodes per gram (wet weight).

EXAMPLE 8

The ability of *Phasmarhabditis* nematodes Produced by Foam Chip Culture to Kill Different Species of Slugs

*Phasmarhabditis* nematodes which had been cultivated on a mixed bacterial flora using methods described in Example 4 were bioassayed against six pest species of slugs. These were *Deroceras reticulatum, D. caruanae, Arion ater, A. intermedius, A. distinctus* and *Tandonia* (Milax) *sowerbyi*. The slugs were collected from bran baited traps at Long Ashton Research Station during November 1990. All slugs were adults except for *A. ater* which were juveniles (mean weight 770 mg). The nematodes were reared in xenic foam-chip bag cultures as described in Example 4. Air dried coarse soil aggregates of diameter 12.5–25 mm which had been obtained by sieving were placed in plastic boxes (135×75×50 mm), with 440 g air-dried soil aggregates per box. Approximately $1.9 \times 10^5$ infective larvae of Phasmarhabditis were added to each of the nematode-treated boxes suspended in 130 ml of tap water. 130 ml of tap water without nematodes was added to the untreated boxes. Ten slugs were placed in each box except for the larger slug species (*T. sowerbyi* and *A. ater*), for which five slugs were kept in each box. Seventeen *A. distinctus* slugs were treated with nematodes and eighteen were kept as untreated controls. For all other species twenty slugs were treated and a further twenty left as untreated controls. The slugs were left in the soil for a five-day infection period after which the soil boxes were dismantled and the number of dead slugs recorded. Surviving slugs were transferred to 9 cm petri dishes lined with moist filter paper where they were kept individually and fed leaf discs of Chinese cabbage. Soil boxes and petri dishes were kept at 10° C. for the duration of each bioassay. Numbers of dead slugs were recorded twice more at three day intervals. Mortalities of individual slug species in treated and untreated cells at any time were compared using a $chi^2$ test. The results are shown in Table 3.

TABLE 3

Percent mortality in different species of slugs 8, 11 and 14 days after treatment with nematodes or being left untreated.

| Slug Species | Day 5 | | Day 8 | | Day 11 | |
| --- | --- | --- | --- | --- | --- | --- |
| | Treated | Un-treated | Treated | Un-treated | Treated | Un-treated |
| *Deroceras reticulatum* | 100 | 10 | 100 | 25 | 100 | 40 |
| *Deroceras caruanae* | 70 | 10 | 100 | 15 | 100 | 20 |
| *Arion ater* | 5 | 0 | 40 | 0 | 100 | 0 |
| *Arion intermedius* | 100 | 40 | 100 | 60 | 100 | 70 |
| *Arion distinctus* | 6 | 6 | 88 | 11 | 100 | 28 |
| *Tandonia sowerbyi* | 20 | 15 | 80 | 15 | 100 | 25 |

After the five day infection period the differences in mortality between nematode-treated and untreated slugs were highly significant ($P<0.001$) for *D. reticulatum, D. caruanae,* and *A. intermedius*. Differences in mortalities between treated and untreated slugs for the other three species were not significant at this stage. After eight days the differences in mortalities between treated and untreated slugs were significant for all species tested ($P<0.001$ for *D. reticulatum, D. caruanae, T. sowerbyi* and *A. distinctus*, and $P<0.01$ for *A. ater*, and *A. intermedius*). By day 11 all slugs treated with nematodes had died. The differences in mortalities between treated and untreated slugs were significant for all species ($P<0.01$ for *A. intermedius* and $P<0.001$ for all other species). The difference was not as great for *A. intermedius* because many of the untreated slugs had died.

It is clear from these results that *Phasmarhabditis* nematodes are capable of killing all the slug species tested.

EXAMPLE 9

The Ability of *Phasmarhabditis nematodes* Produced by Foam Chip culture to Control Plant Damage Caused by the Field Slug *Deroceras reticulatum* Under Field Conditions A mini-plot field experiment was carried out to compare slug damage to Chinese cabbage seedlings in untreated plots, plots treated with methiocaro pellets (generally considered to be the best available chemical for slug control) and plots treated with a single high dose of nematodes produced by foam chip culture with a mixed bacterial flora as described in Example 3. The test was done in a series of 40 micro-plots containing a loam soil on a bed of coarse gravel. The plots were 70×70×30 cm deep and were separated by either wood or concrete barriers, surmounted by a fence, 10 cm high, of 0.8 mm woven copper mesh to act as a barrier to slug movement between plots.

Thirty-six of the plots were populated with slugs between March and June 1989. No slugs were added to the remaining 4 plots which were used as a measure of the resident slug population. Five field-collected adult *D. reticulatum* were added to each of the plots to be populated. These slugs had been kept in quarantine boxes for at least two weeks to ensure they were not carrying any parasites. Thirty-four laboratory reared neonate *D. reticulatum* were added to each plot throughout the three-month period so that at the start of the experiment slugs at many stages of development were present.

The experimental design consisted of nine replicates of four randomized blocks, each block consisting of two untreated plots, one plot treated with nematodes and one plot treated with methiocarb pellets.

$1.05 \times 10^6$ nematodes were suspended in 900 ml of tap water and drenched over each plot using a watering can fitted with a rose. A further 100 ml of tap water was used to rinse the can out and then poured onto the plots. One liter of tap water was also added to the untreated and methiocarb-treated plots. Methiocarb pellets were added at the recommended field rate (5.5 kg/ha=0.275 g/plot). The pellets were weighed out and distributed evenly over the plots by hand. The plots were irrigated from an overhead pipe throughout the course of the experiment, to ensure that conditions were favourable for slug activity.

At the start of the experiment, young Chinese cabbage seedlings which had been grown in a glasshouse were planted out, nine seedlings in each plot arranged in a 3×3 square. These were examined twice weekly and the amount of slug damage to each seedling was estimated to the nearest 5 percent.

Two weeks after planting, the seedlings in some of the untreated plots were completely destroyed, so remnants of the old seedlings were removed from all the plots and new ones planted. This was repeated after a further two weeks. After two more weeks the experiment was finished (six weeks in total). Seedling damage was recorded twice weekly throughout the course of the experiment. The copper mesh barriers between plots in one of the treatment blocks (Block 9) became detached after the first four weeks allowing slug movement between plots, so these plots were ignored and the results shown for the fifth and sixth weeks represent only 8 blocks.

At the end of the experiment two soil samples 25×25×10 cm deep were taken from each plot of the remaining 8 blocks, one sample being taken from the middle and one from the South East corner of each plot. The samples were gradually flooded over nine days in the LARS slug extraction unit (Glen & Wiltshire, in Proceedings 1986 British Crop Protection Conference (1986), vol 1, pp 139–144), and the slugs were removed from the surface daily.

The amount of slug damage to the seedlings in each treatment during the course of the experiment is shown in FIG. 1.

Analysis of variance following angular transformation to stabilise the variance shows that both methiocarb pellets and the nematode significantly ($\underline{P}<0.001$) reduced the amount of slug damage to seedlings. At the first reading (four days after treatment) there was significantly ($\underline{P}<0.05$) more damage in the plots treated with nematodes than in plots treated with methiocarb, but as the seedlings outgrew the initial damage the difference between the nematode and methiocarb treated plots narrowed. By the end of the first week the nematode treated plots showed less damage than the methiocaro treated plots, but this difference was not significant. After 17 days (first examination of the second batch of seedlings) the nematode treated plots had significantly less ($\underline{P}<0.05$) damage than the methiocarb treated plots, and this persisted ($\underline{P}<0.01$) until the end of the experiment.

Three species of slugs were found in the soil samples, *Deroceras reticulatum*, *Deroceras caruanae* and *Boettgerilla pallens*. In all plots, only 2 *D. caruanae* were found, but 89 *B. pallens* were found compared with 55 *D. reticulatum*. The *B. pallens* were presumably introduced into the plots some time previously and had reproduced and colonised them throughout. The preferred diet of this slug is not known but in laboratory tests it did not damage Chinese cabbage leaves during three weeks exposure without any alternative food source. It is therefore unlikely that this slug was causing damage to the seedlings in this trial.

No *D. reticulatum* were found in soil samples from the four plots to which none was added. This suggests that unlike *B. pallens* there were few if any *D. reticulatum* in the plots before the start of the experiment.

Figure 2:
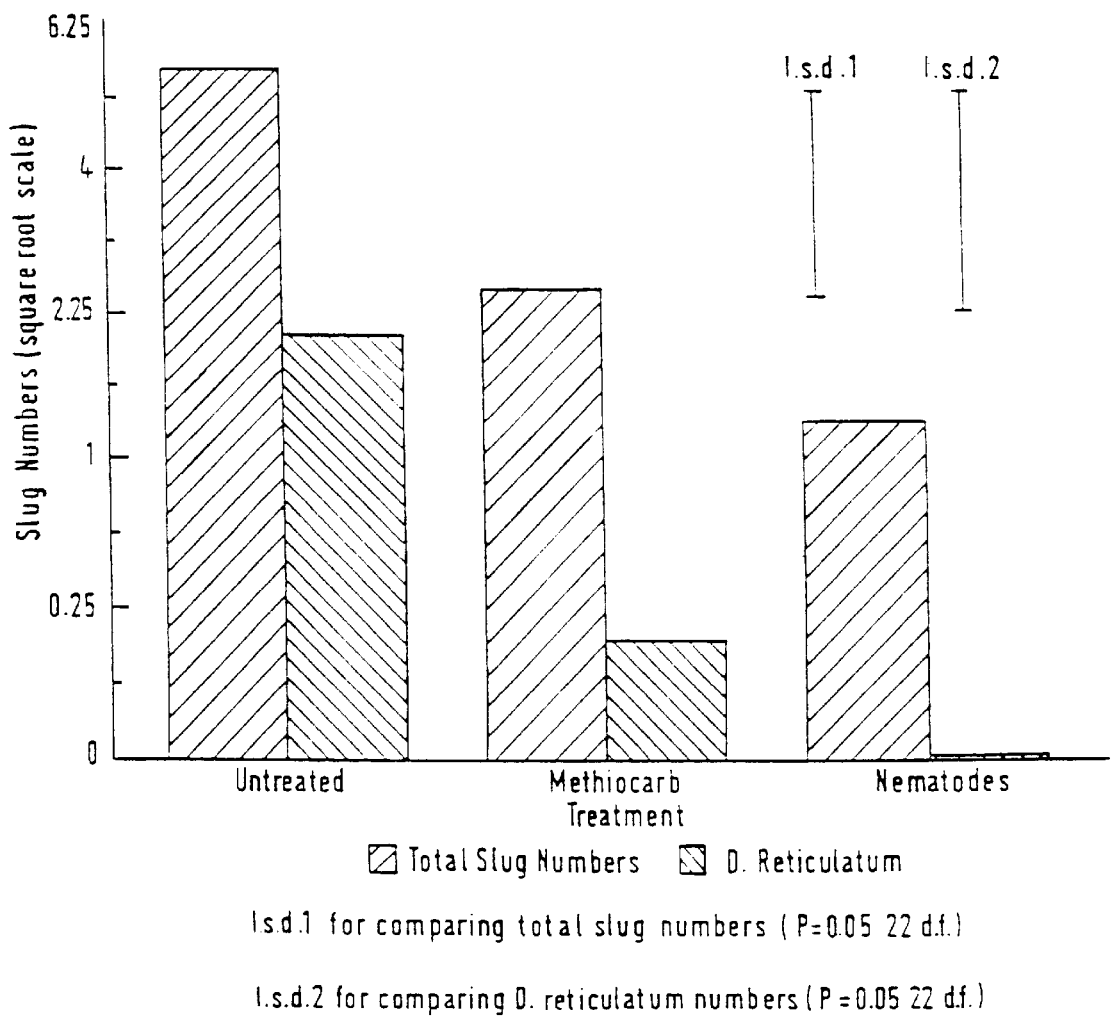
FIG. 2 is a bar graph illustrating the effects of *Phasmarhabditis* nematodes on slugs and *Deroceras reticulatum* in field experiments.

Total slug numbers and biomass extracted from the different treatments were transformed to square roots for statistical analysis. The results are shown in FIG. 2.

Significantly fewer slugs were extracted from nematode-treated than from untreated plots ($\underline{P}<0.01$ for all slug species and for *D. reticulatum* alone) and fewer were extracted from methiocarb-treated than from untreated plots ($\underline{P}<0.05$ for all slug species and for *D. reticulatum* alone). Although fewer slugs were extracted from nematode-treated plots than from those treated with methiocarb, this difference was not significant. No *D. reticulatum* were extracted from the nematode-treated plots suggesting that this species had been almost eliminated from these plots. The numbers of *B. pallens* were not significantly affected by nematodes or methiocarb although fewer *B. pallens* were found in nematode-treated plots than untreated plots.

EXAMPLE 10

The Ability of Monoxenic *Phasmarhabditis nematodes* to Kill Different Species of Mollusc Pests Monoxenic *Phasmarhabditis nematodes*, which had been grown in association with *M. osloensis* strain 48 as described in Example 5, were bioassayed against various mollusc pest species, including *Monacha cantiana* (the Kentish snail), as described in Example 8. The results are shown in Table 4.

TABLE 4

Percent mortality in different species of pest mollusc after treatment with monoxenic nematodes or being left untreated

| Mollusc Species | Duration of Bioassay (days) | Treated | Untreated |
|---|---|---|---|
| Deroceras reticulatum | 11 | 100 | 15 |
| Deroceras caruanae | 11 | 100 | 10 |
| Monacha cantiana | 5 | 100 | 0 |
| Arion intermedius | 5 | 100 | 0 |
| Arion distinctus | 11 | 100 | 0 |
| Tandonia sowerbyi | 11 | 70 | 5 |

The differences in mortalities between treated and untreated molluscs were significant for all species tested ($P<0.001$), indicating that all the species of mollusc pest tested were susceptible to Phasmarhabditis sp. monoxenised with *M. osloensis* strain 48. The activity spectrum of monoxenic nematodes is unaltered in comparison to xenic nematodes.

Figure 3:
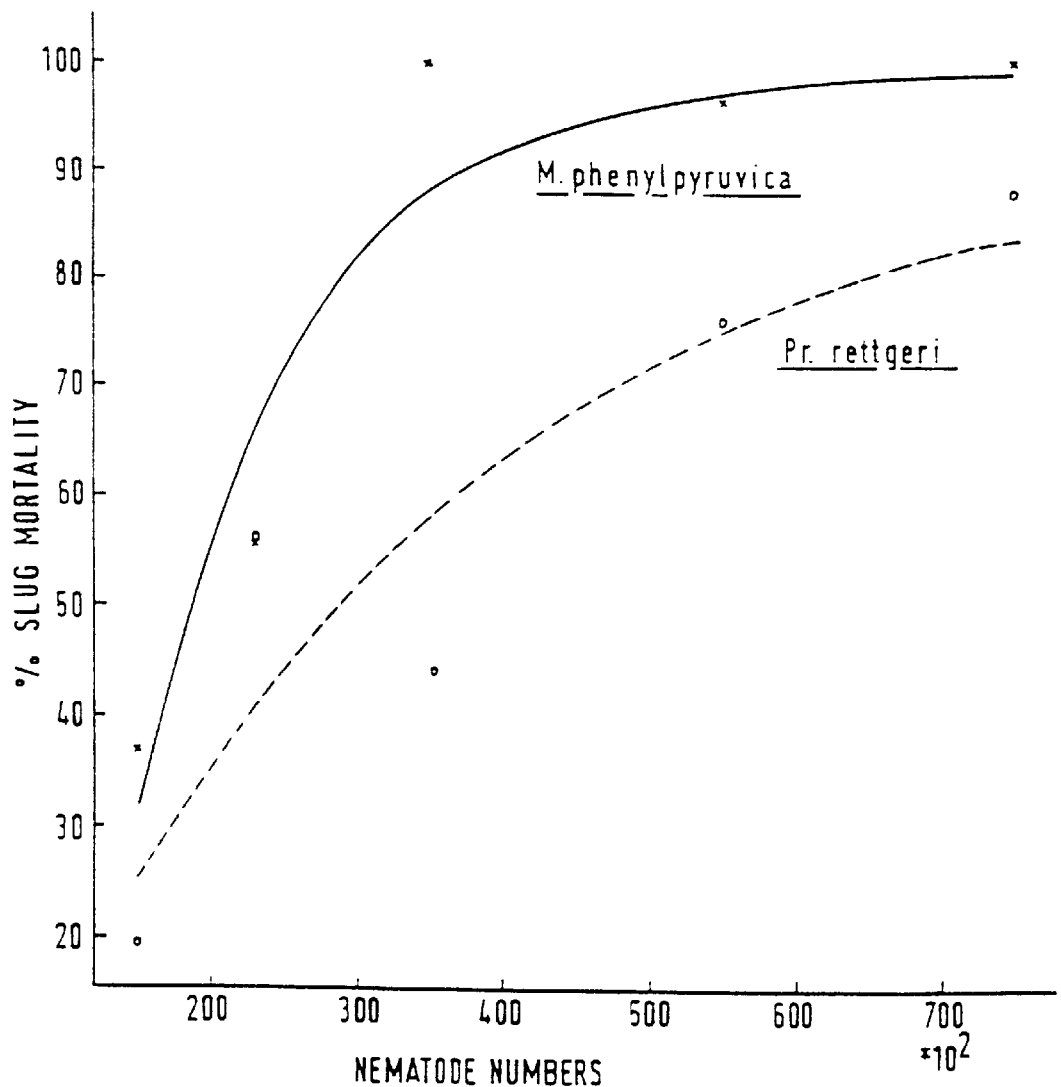
FIG. 3 is a graph illustrating a bioassay of *Phasmarhabditis* nematodes associated with *M. osloensis* or *P. rettgeri* atainst *D. reticulatum*.

Monoxenic *Phasmarhabditis nematodes* were grown in association with *M. osloensis* or *P. rettgeri* as described in Example 5, and bioassayed at various dose rates against the slug species *D. reticulatum* as described in Example 8. The results are summarised in FIG. 3. Both types of monoxenic nematode are active against *D. reticulatum*.

EXAMPLE 11

The Ability of Monoxenic *Phasmarhabditis nematodes* to Control Plant Damage Caused by the Field Slug *Deroceras reticulatum* Under Field Conditions A field trial was carried out to compare slug damage to winter wheat (cv Mercia) in untreated plots, plots treated with methiocarb pellets and plots treated with a range of nematode doses. Monoxenic nematodes were produced in association with *M. osloensis* strain 48 as described in Example 5 and formulated in clay, as described in Example 7. as a water-dispersable powder containing $0.36 \times 10^6$ nematodes per gram (wet weight). Nematodes were applied immediately after seed sowing as an aqueous spray in a volume equivalent to 1,100 liters/hectare. Methiocarb pellets were applied by hand at the recommended field rate (5.5 kg/hectare).

Surface traps and soil samples were used to monitor the slug population in the field trial plots. Many different species of slugs, including *Deroceras reticulatum, Arion silvaticus, Arion subfuscus, Arion ater, Tandonia sowerbyi* and *Milax gagates* were found in the plots, but *D. reticulatum* was by far the predominant species.

Six weeks after sowing, plots were assessed for wheat seedling emergence, which is an estimate of lethal slug damage (i.e. a reduction in plant stand), and estimates were made of sublethal slug damage (i.e. plant grazing by slugs) by visual assessment of randomly selected plants. The mean numbers of emerged wheat plants per 0.5 m length of drill row for the different treatments are shown in Table 5.

TABLE 5

Mean numbers of emerged wheat plants per 0.5 m length of drill row for the various treatments in the field trial (assessments made 6 weeks after sowing)

| Treatment | Mean Numbers of Emerged Plants |
|---|---|
| Untreated | 12.93 |
| Nematode dose $1 \times 10^8$ per ha | 12.78 |
| Nematode dose $3 \times 10^8$ per ha | 13.95 |
| Nematode dose $1 \times 10^9$ per ha | 13.25 |
| Nematode dose $3 \times 10^9$ per ha | 14.88 |
| Nematode dose $1 \times 10^{10}$ per ha | 16.50 |
| Methiocarb | 14.57 |

S.E.D. = 1.314, (399 d.f.)

There is a clear increase in the numbers of emerged plants with increased nematode dose, hence the nematode treatments caused a reduction in lethal slug damage.

The data on mean percentage of leaf area damaged by slugs were transformed to angles prior to analysis. The results are shown in Table 6.

TABLE 6

Mean angular percentage leaf area damaged by slugs per plant for the various treatments in the field trial (assessments were made 6 weeks after sowing)

| Treatment | Mean Angular Percentage Leaf Area Damaged Per Plant |
|---|---|
| Untreated | 31.82 |
| Nematode dose $1 \times 10^8$ per ha | 29.15 |
| Nematode dose $3 \times 10^8$ per ha | 28.87 |
| Nematode dose $1 \times 10^9$ per ha | 22.11 |
| Nematode dose $3 \times 10^9$ per ha | 18.63 |
| Nematode dose $1 \times 10^{10}$ per ha | 16.49 |
| Methiocarb | 25.17 |

S.E.D. = 3.395, (24 d.f.)

There were significant differences in the area of leaf damaged by slugs between treatments ($P<0.001$) with plants treated with the highest three nematode doses having significantly ($P<0.01$) less slug damage than plants from the untreated plots. Plants from plots treated with the highest dose of nematodes had significantly ($P<0.05$) less slug damage than plants from the methiocarb-treated plots. Thus the nematodes are able to give good control of sub-lethal slug damage.

EXAMPLE 12

The Ability of Monoxenic *Phasmorhabditis nematodes* to Kill the Aquatic Snail *Lymnaea stagnalis*

Monoxenic nematodes were produced in association with *M. osloensis* strain 48 as described in Example 5 and formulated in clay, as described in Example 7. as a water-dispersable powder containing approximately $0.36 \times 10^6$ nematodes per gram (wet weight). Ten individuals of the aquatic snail *Lymnaea stagnalis* were added to each of five clean fish tanks which were half-filled with pond water containing some aquatic plants which served as a food source for the snails. The tanks were aerated using a small air pump and maintained at 15° C.

To each of the four tanks approximately $6 \times 10^6$ nematodes were added in the form of the water-dispersable powder formulation. No nematodes were added to the fifth tank which served as a control. After three days incubation, average snail mortality in the nematode-treated tanks was 45%, rising to 100% after six days. There was no mortality in the untreated control tank after six days incubation.

We claim:

1. A composition for the control of molluscs comprising an effective amount of infective dauer larvae of *Phasmarhabditis nematodes* that have been cultured with a nematode growth promoting and pathogenicity-inducing bacterium, and a suitable carrier or encapsulation agent.

2. A composition according to claim 1, in which the nematodes are *Phasmarhabditis neopapillosa* or *Phasmarhabditis hermaphrodita*.

3. A composition according to claim 1, in which the growth-promoting bacterium is selected from the group consisting of:

*Pseudomonas fluorescens,*
*Providencia rettgeri,*
*Serratia proteomaculans,*
*Aeromonas salmonicida,*
*Moraxella phenylpyruvica,*
*Bacillus cereus,*
*Flavobacterium odoratum,*
*Flavobacterium brevi.*

4. A composition according to claim 3, in which the growth-promoting bacterium is a biologically pure culture of *Moraxella osolensis* strain NCIMB 40508 or a biologically pure culture of *Pseudomonas fluorescens* strain NCIMB 40509.

5. A composition according to claim 1, in which the carrier is a clay.

6. A composition according to claim 1 in the form of a water-dispersable powder, wherein the carrier is calcium montmorillonite clay, and the nematode concentration is from $0.1 \times 10^6$ to $2.0 \times 10^6$ per gram of total composition (wet weight).

7. A composition according to claim 6, wherein the nematode concentration is from $0.3 \times 10^6$ to $0.8 \times 10^6$ per gram of the total composition (wet weight).

* * * * *